United States Patent [19]

Fife et al.

[11] Patent Number: 5,668,122

[45] Date of Patent: Sep. 16, 1997

[54] METHOD TO TREAT CANCER WITH TETRACYCLINES

[76] Inventors: Rose S. Fife, 5 Smith La., Zionsville, Ind. 46077; George W. Sledge, 612 King Dr., Indianapolis, Ind. 46260

[21] Appl. No.: 431,751

[22] Filed: May 1, 1995

Related U.S. Application Data

[63] Continuation of Ser. No. 98,137, Jul. 28, 1993, abandoned.

[51] Int. Cl.$^6$ ..................................................... A61K 31/65
[52] U.S. Cl. ............................................................ 514/152
[58] Field of Search ............................................... 514/152

[56] References Cited

U.S. PATENT DOCUMENTS

| | | | |
|---|---|---|---|
| 4,791,991 | 12/1988 | Umemura et al. | 514/532 |
| 5,045,538 | 9/1991 | Schneider et al. | 514/152 |
| 5,321,017 | 6/1994 | Golub et al. | 514/152 |

OTHER PUBLICATIONS

Tamargo, R.J., Bok, R.A. and Brem, H., "Angiogenesis Inhibition by Minocycline," 51 *Cancer Research* 672 (Jan. 15, 1991).

Golub, L.M., Ciancio, S., Ramamurthy, N.S., Leung, M., McNamara, T.F., "Low-dose doxycycline therapy: Effect on gingival and crevicular fluid collagenase activity in humans," 25 *J. Periodont. Res.* 321 (1990).

Ramamurthy, N.S., Vernillo, A.T., Lee, H.-M., Golub, L.M., Rifkin, B.R., "The Effect of Tetracyclines on Collagenase Activity in UMR 106-01 RAT Osteoblastic Osteosarcoma Cells," *Res. Comm. in Chem. Pathol. and Pharmac.*, vol. 70, No. 3, pp. 323-335 (Dec. 1990).

van der Bogert, C., Dontje, B.H.J., Holtrop, M., Melis, T.E., Romijn, C., van Dongen, J.W., Kroon, A.M., "Arrest of the Proliferation of Renal and Prostate Carcinomas of Human Origin by Inhibition of Mitochondrial Protein Synthesis," 46 *Cancer Research* 3283 (Jul. 1986).

Zucker, S., Lysik, R.M., Ramamurthy, N.S., Golub, L.M., Wieman, J.M., Wilkie, D.P., "Diversity of Melanoma Plasma Membrane Proteinases: Inhibition of Collagenolytic and Cytolytic Activities by Minocycline," *JNCI*, vol. 75, No. 3, pp. 517-525 (Sep. 1985).

Golub, L.M., Lee, H.M., Lehrer, G., Nemiroff, A., McNamara, T.F., Kaplan, R., and Ramamurthy, N.S., "Minocycline reduces gingival collagenolytic activity during diabetes," 18 *J. of Periodont. Research* 516 (1983).

*Primary Examiner*—Jerome D. Goldberg
*Attorney, Agent, or Firm*—Macheledt Bales & Johnson LLP

[57] ABSTRACT

The present invention provides a method to treat susceptible cancers in humans comprising administering a cancer-treating amount of a member of the tetracycline family or a pharmaceutically acceptable salt thereof. Doxycycline, minocycline and tetracycline are utilized in the preferred method. Preferred methods of the present invention treat osteo-, breast, lung, prostate or Kaposi's cancers. Other aspects of the invention are described in the full application.

12 Claims, No Drawings

METHOD TO TREAT CANCER WITH TETRACYCLINES

This application is a continuation of application Ser. No. 08/098,137, filed Jul. 28, 1993, now abandoned.

BACKGROUND OF THE INVENTION

Cancer is a leading cause of death in the United States. Breast, lung and prostate cancer alone cost billions of medical dollars each year. Most treatments now available are quite toxic to the human body; side effects such as nausea, vomiting, hair loss and fatigue cause hesitance and fear in cancer patients facing such treatments. The present invention provides a relatively non-toxic and simple treatment for cancers. This invention discloses a method to treat cancers by administering a member of the tetracycline family (TCN).

The major cause of cancer morbidity and mortality in humans is metastatic disease. As a consequence, there has been much interest in the mechanisms involved in invasion of cells and metastasis. Several enzyme systems have been implicated in the metastatic process: metalloproteinases, cysteine proteases, and serine proteinases. Yagel, S.A. et al., 49 *Cancer Research* 3553 (1989), Dickson R. B., 41 J. *Steroid Biochem. Molec. Biol.* 389 (1992) and Zucker S. et al., 45 *Cancer Research* 6168 (1985). Inhibitors of metalloproteinases, especially of the collagenases, have been the focus of intense study. DeClerck A. et al., 52 *Cancer Research* 701 (1992).

TCNs have been shown in dental studies to suppress metalloproteinase activity in gingiva, bone and cartilage. Golub L. M. et al., 25 *J. Periodontal Res.* (1990) and Gomes B. C. et al., 40 *Experentia* 1273 (1984). A few studies on animals have indicated that minocycline, a TCN, can suppress tumor metalloproteinase activity in animals. Zucker S. et al., 75 (3) JNCI 517 (1985). Other studies in animals show suppression of angiogenesis upon administration of minocycline. Tamargo R. J. et al., 51 *Cancer Research* 672 (1991). In 1986, researchers investigated human renal and prostate cancer cell proliferation arrest upon administration of doxycycline, particularly focusing on the effect of doxycycline on mitochondrial function. van de Bogert et al., 6 *Cancer Res.* 3283 (1986).

The present invention discloses that growth, migration and enzyme activity of human cancer cells can be altered by administration of TCNs. This invention provides a simple, non-toxic treatment for cancers.

SUMMARY OF THE INVENTION

The present invention provides a method to treat susceptible cancers in humans comprising administering a cancer-treating amount of a TCN or a pharmaceutically acceptable salt thereof. Preferably, a present method utilizes doxycycline, minocycline or tetracycline as the TCN administered.

Also provided is a method which treats metastatic cancers. Preferably, a present method to treat metastatic cancers utilizes doxycycline, minocycline or tetracycline as the TCN administered.

Moreover, a method to treat susceptible cancers in humans comprising administering a TCN wherein the TCN is administered as an adjuvant is provided. A method wherein the adjuvant therapy is chemotherapy is preferred. More preferred is an adjuvant therapy chosen from the group consisting of cytoxan, vincristin, and doxorubicin. However, also more preferred is an adjuvant therapy chosen from the group melphalan and tamoxifen.

Another aspect of the present invention is a method as disclosed which utilizes oral or intravenous administration.

A method wherein the TCN is administered prophylactically is also provided.

Preferably, the present method will be utilized to treat osteosarcoma, breast carcinoma, lung carcinoma, prostate carcinoma or Kaposi's sarcoma.

The following section provides a more detailed description of the present invention. For purposes of clarity and as to aid understanding of the invention, as disclosed and claimed herein, the following abbreviation is defined below.

"TCNs" or TCN—a member of the tetracycline family including, but not limited to, tetracydine, ninocydine, doxycydine, oxytetracycline, chlortetracycline, demedotetracycline, 6-alphabenzylthiomethylenetetraccycline, 6-fluoro-6-demethyltetracycline, the mono-N-alkylated amide of tetracycline, and 11 alpha-chlorotetracycline, minocycline, 7-chloro-tetracycline, 4-de(dimethylamino) tetracycline, 4-de (dimethylamino)-5-oxytetracydine, 4-de (dimethylamino)-7-chlorotetracycline, 6-alpha-deoxy-5-hydroxy-4-dedimethylamino-tetracydine, 7-chloro-6-demethyl-4-dedimethylamino-tetracycline, 4-hydroxy-4dedimethylaminotetracydine or any chemical compound which has substantially the same structure and substantially the same function.

DETAILED DESCRIPTION OF THE INVENTION

The present invention provides a method to treat susceptible cancers in humans comprising administering a cancer-treating amount of a TCN or a pharmaceutically acceptable salt thereof. Preferably, a present method utilizes doxycycline, minocycline or tetracycline as the TCN administered. Those in the art recognize that tetracyclines are available in many commerdal forms from pharmaceutical companies. Even if the particular salt form or formulation is not readily available, those in the art will recognize that alteration of salt forms or formulations are well known procedures. Moreover, diagnosis of cancer and the determination of the appropriate treatment is within the skill of those in the art. Furthermore, artisans will recognize that both antimicrobial and non-antimicrobial TCNs are useful in the present invention.

Also provided is a method to treat metastatic cancers. Preferably, a present method to treat metastatic cancers utilizes doxycycline, minocycline or tetracycline as the TCN administered.

Moreover, a method to treat susceptible cancers in humans comprising administering a TCN wherein the TCN is administered as an adjuvant is provided. A method wherein the adjuvant therapy is chemotherapy is preferred. However, combination of TCN therapy with radiotherapy, thermotherapy, laser therapy is also considered part of the present invention. More preferred is an adjuvant therapy chosen from the group consisting of cytoxan, vincristin, and doxorubicin. However, also more preferred is an adjuvant therapy chosen from the group melphalan and tamoxifen For example, a prophylactic application of the present invention comprises administering the therapy to women who have a family history of breast cancer, even if no breast cancer is found at the time of administration of the therapy.

Another aspect of the present invention is a method as disclosed which utilizes oral or intravenous administration.

However, those in the art will recognize that many avenues of administration are possible. For instance, administration of drug may be via capsule, tablet, solution, sachet, suspension, intravenously, orally, intramuscularly, including implantation into the tumor itself, topically or parenterally.

A method wherein the TCN is administered prophylactically is also provided. Those in the art recognize certain hereditary or environmental situations wherein a person may be predisposed to cancer: In those cases, or to provide peace of mind for persons concerned about developing cancer, artisans may choose to administer TCNs prophylactically. This is another embodiment of the present invention.

Further, in another embodiment of the present invention, a method wherein the cancer-treating amount is 100 milligrams per day is provided. The method preferrably utilizes. 1 mg/kg per day to 30 mg/kg/day. Most preferable, however, is a method which utilizes 2 mg/kg per day–15 mg/kg per day. The best method utilzes 100 mg daily. However, skilled artisans recognize that dosage will vary according to accepted variables such as weight and condition of the patient. Preferrably, the present method will be utilized to treat osteosarcoma, breast carcinoma, lung carcinoma, prostate carcinoma or Kaposi's sarcoma. However, any cancer can be treated with the present invention, including, for example, chondrosarcoma, fibrosarcoma, ovarian carcinoma, melanoma and desmold tumors.

EXAMPLES

The following are examples of the present invention. These examples are not intended to limit the scope of the application.

Example 1

Murine lung carcinoma cells were obtained from the American Type Culture Collection (ATCC), 12301 Parklawn Drive, Rockville, Md., 20852-1776. MDA-MB-435 human breast carcinoma cells, were obtained from Dr. Janet Price at the Department of Cell Biology at the University of Tex., M.D. Cancer Center, HMB-173, 1515 Holcombe Boulevard, Houston, 7030. The MDA-MB-435 human breast cancer/nude mouse xenograft model system was originally described by Price et al., 50 Cancer Research 717 (1990).

Example 2

$4 \times 10^4$ murine Lewis lung carcinoma cells were layered on a matrix of Matrigel™ (available from Collaborative Biomed, Bedford, Mass.) in conditioned medium. Migration through the Matrigel™ matrix by the murine Lewis lung carcinoma cells was examined both in the presence and absence of 10 µg/ml of doxycycline hycate (obtained from Elkins-Sinn, of Cherry Hill, N.J.). For those cells which were grown in the presence of doxycycline, doxycycline was added daily. Migration was measured by counting cells at the bottom of the wells 7 days after the experiment began.

The untreated controls showed an average penetration of $8.45 \times 10^4$ cells through the matrix, while $5.1 \times 10^3$ of the doxycycline-treated cells migrated. Skilled artisans will recognize that this is a dramatic decrease in cancerous cell migration.

Example 3

$4 \times 10^4$ MDA-MB 435 breast cancer cells were layered on a matrix of Matrigel™ and conditioned medium. Migration through the Matrigel™ matrix by the breast cancer cells was examined both in the presence and absence of doxycycline. Migration of both sets of cells was measured by counting cells at the bottom of the wells 5 days after the experiment began.

The untreated controls demonstrated an average migration of $3.57 \times 10^4$ cells through the wells, while an average of $4.5 \times 10^3$ doxycycline-treated cells migrated. Skilled artisans will recognize that this is a dramatic decrease in cancerous cell migration.

Example 4

$1 \times 10^4$ MDA-MB 435 cells were layered as described in Example 3, except that 5 µg/ml doxycycline was added daily. Migration of both sets of cells was measured by counting cells at the bottom of the wells 9 days after the experiment began.

The untreated controls demonstrated migration of $1.4 \times 10^3$ cells through the wells, while wells to which 5 µg/ml doxycycline was added daily revealed migration of $0.75 \times 10^3$ cells. Skilled artisans will recognize that this is a dramatic decrease in cancerous cell migration.

Example 5

$1 \times 10^4$ MDA-MB 435 cells were layered as described in Example 4, except that 10 µg/ml doxycycline was added daily. Migration of both sets of cells was measured by counting cells at the bottom of the wells 9 days after the experiment began.

In wells to which 10 µg/ml of doxycycline was added daily, $0.042 \times 10^3$ cells migrated. Skilled artisans will recognize that this is a dramatic decrease in cancerous cell migration.

Example 6

MDA-MB 435 human breast cancer cells were plated in 35 mm wells of Costar™ 6-well plates at a concentration of $10^5$ cells per well. Medium (with or without doxycycline at a concentration of 10 µg/ml) was replaced daily, beginning on day 1 following plating. Cells were harvested with trypsin-EDTA on days 2, 4 and 6 following initial plating. The cells were then counted in a hemocytometer. Each time point employed a sample size of 6 wells.

In the cells that were grown in the presence of doxycycline, the rate of growth at the end of 6 days was about 30–40 percent less than those cells grown in the absence of doxycycline. Skilled artisans will recognize that this is a dramatic decrease in cancerous cell growth.

Gelatin zymography revealed significant suppression (greater than 50%) of gelatinolytic activity by 10 µg/ml of doxycycline in the breast carcinoma cell line. Five µg/ml of doxycycline of doxycycline produced only minimal suppression of gelatinolytic activity.

Example 7

Experiments similar to Example 6 were performed using the human prostate adenocarcinoma cells LNCaP.FGC from the American Type Culture Collection. Treated cells (10 µg/ml or 5 µg/ml of doxycyline) showed a reduction in growth by approximately two orders of magnitude over the controls, as early as three days after the experiment was initiated.

Gelatin zymography revealed significant suppression (greater than 50%) of gelatinolytic activity by 10 µg/ml of doxycycline in the prostate adenosarcoma cell line. Five μg/ml of doxycyelilne of doxycycline produced only minimal suppression of gelatinolytic activity.

Example 8

A human osteosarcoma cell line (U2OS) was obtained from the American Type Culture Collection, and another human osteosarcoma cell line (HO1) was grown by resecting cells from a tumor and growing as is standard. The HO1 cells were incubated in the presence of 10 μg/ml of doxycycline for 6 days, and samples were obtained every 2 days. A 6-fold suppression of cell growth in the doxycycline-treated cells over the untreated controls was obxerved. In the presence of 5 μg/ml of doxycycline, a 3-fold suppression of cell growth was observed. In the U2OS cells, 10 μg/ml of doxycycline produced a 4-fold suppression of cell proliferation and 5 μg/ml of doxycycline produced no suppression when compared with the untreated controls.

Gelatin zymography revealed significant suppression (greater than 50%) of gelatinolytic activity by 10 μg/ml of doxycycline in both osteosarcoma cell lines. Five μg/ml of doxycycline of doxycycline produced only minimal suppression of gelatinolytic activity.

A skilled artisan would recognize that these results indicate that a concentration of at least 10 μg/ml doxycycline will supress osteosarcoma cell proliferation as well as gelatinolytic activity.

We claim:

1. A method to inhibit migration of TCN-sensitive cancer cells without curing the underlying tumor in a human who has identified cancer and is in need of cell migration inhibition, comprising administering to said human a cell migration-inhibiting amount of a tetracycline (TCN) or a pharmaceutically acceptable salt thereof.

2. A method of claim 1, wherein the TCN administered is doxycycline.

3. A method of claim 1, wherein the TCN administered is minocycline.

4. A method of claim 1, wherein the TCN administered is tetracycline.

5. A method of claim 1, wherein the TCN is administered orally.

6. A method of claim 1, wherein the TCN is administered via implantation.

7. A method of claim 1, wherein the identified cancer is osteosarcoma.

8. A method of claim 1, wherein the identified cancer is breast carcinoma.

9. A method of claim 1, wherein the identified cancer is lung carcinoma.

10. A method of claim 1, wherein the identified cancer is prostate carcinoma.

11. A method of claim 1, wherein the identified cancer is Kaposi's sarcoma.

12. A method for treating a human genetically or environmentally susceptible to migration of TCN-sensitive cancer cells, comprising administering to said human a cancer cell migration-preventing amount of a tetracycline (TCN) or a pharmaceutically acceptable salt thereof without curing the underlying tumor.

* * * * *